(12) United States Patent
Margot

(10) Patent No.: US 10,080,536 B2
(45) Date of Patent: Sep. 25, 2018

(54) SUPPLY DEVICE AND METHOD FOR A MOBILE IMAGING DEVICE

(71) Applicant: GENERAL ELECTRIC COMPANY, Schenectady, NY (US)

(72) Inventor: Paul Vincent Margot, Buc (FR)

(73) Assignee: General Electric Company, Schenectady, NY (US)

( * ) Notice: Subject to any disclaimer, the term of this patent is extended or adjusted under 35 U.S.C. 154(b) by 488 days.

(21) Appl. No.: 14/958,569

(22) Filed: Dec. 3, 2015

(65) Prior Publication Data

US 2016/0228080 A1   Aug. 11, 2016

(30) Foreign Application Priority Data

Dec. 3, 2014   (GB) .................................. 1421493.6

(51) Int. Cl.
*A61B 5/00* (2006.01)
*A61B 6/00* (2006.01)
*A61B 6/10* (2006.01)
*A61B 6/04* (2006.01)

(52) U.S. Cl.
CPC ............ *A61B 6/4441* (2013.01); *A61B 6/102* (2013.01); *A61B 6/4405* (2013.01); *A61B 6/507* (2013.01); *A61B 6/0407* (2013.01)

(58) Field of Classification Search
CPC ....... A61B 6/4441; A61B 6/102; A61B 6/507; A61B 6/4405; A61B 6/0407
See application file for complete search history.

(56) References Cited

U.S. PATENT DOCUMENTS

| 2004/0183683 A1 | 9/2004 | Funahashi |
| 2009/0065596 A1 | 3/2009 | Seem et al. |
| 2009/0177079 A1* | 7/2009 | Jauster .................. A61B 5/055 600/420 |

(Continued)

FOREIGN PATENT DOCUMENTS

| CN | 103985050 A | 8/2014 |
| JP | 2002291895 A | 10/2002 |
| WO | 2012093801 A2 | 7/2012 |

OTHER PUBLICATIONS

Combined Search and Exam Report for corresponding GB Appln. No. 1422827.4 dated Jun. 15, 2015, 10 pages.

*Primary Examiner* — Joel Lamprecht
(74) *Attorney, Agent, or Firm* — GE Global Patent Operation; Marc A. Vivenzio

(57) ABSTRACT

A device and method are provided for supplying a medium to an object of interest, such as a patient to be scanned for image acquisition. The device comprises an arc-shaped member and a support for said arc-shaped member, wherein the arc-shaped member is configured to support a radiation source on one end and a detector on another end to scan the object of interest, and the support comprises a gantry with a rotatable support arm supporting the arc-shaped member. The device further comprises at least one medium supply unit mounted on the gantry. The supply unit is connectable to a cable that is guided in the vicinity or in the region of the axis of rotation of the support arm so that the object of interest can be supplied with a perfusion or any other medium, while enabling the mobile imaging device to rotate around the patient to acquire x-ray images.

17 Claims, 7 Drawing Sheets

(56) References Cited

U.S. PATENT DOCUMENTS

| | | | |
|---|---|---|---|
| 2010/0063514 A1* | 3/2010 | Maschke | A61B 5/1135 606/130 |
| 2010/0141437 A1 | 6/2010 | Karam et al. | |
| 2011/0178359 A1* | 7/2011 | Hirschman | G21F 5/015 600/4 |
| 2012/0114217 A1* | 5/2012 | Mistretta | A61B 6/4441 382/133 |
| 2013/0073405 A1 | 3/2013 | Ariyibi | |

* cited by examiner

SUPPLY DEVICE AND METHOD FOR A MOBILE IMAGING DEVICE

BACKGROUND

Healthcare practice has shown the value of taking images as x-rays of a patient from a number of different positions. The use of medical imaging acquisition systems has improved the diagnosis and care of patients. Currently available x-ray imaging systems can be used in operating rooms, intensive care departments or emergency rooms. One type of device uses a mobile C-arm which is rotated to provide the necessary scanning views. Mobile C-arm x-ray diagnostic equipment has been developed to enable a physician to treat or otherwise attend to the patient without the need to repeatedly remove and replace the x-ray equipment. More particularly, mobile C-arm x-ray equipment has been developed for surgical and other interventional procedures. Mobile C-arm x-ray image acquisition devices can be used for well-defined surgical planning and guiding surgical interventions. During surgeries the space immediately surrounding the patient should not be unduly encumbered in order to enable a safe access of the physician to the patient.

In the following the term C-arm refers to an elongated arc-shaped member terminating in opposing distal ends. An x-ray source and detector are mounted at or near the distal ends of the C-arm. The so called C-arm is mounted on a support arm such that a rotational movement of the arm together with the C-arm is enabled. The C-arm is adjustable in at least two degrees of freedom. In other words, the C-arm is movable in an angular direction and in an orbital direction. For the orbital movement the C-arm can be displaced by a suitable sliding mechanism integrated in the support structure. Based on the angular and orbital movement capabilities images can be sequentially and/or continuously obtained in different planes. The x-ray source and the image receptor can be selectively orientated on a vertical axis, on a horizontal axis or somewhere in between. The circular rotation of the C-arm and thus of imaging acquisition device allows the physician to take x-ray images of a patient at a desired angle with respect to the particular anatomical condition, which needs to be imaged.

Users of C-arm x-ray imaging systems are faced with a number of challenges. Since the C-arm needs to rotate around the patient there is the risk that objects as a supply cable connected to the patient collide or gets entangled with the x-ray source or the x-ray detector. However, in the case that the supply cable is configured for continuous perfusion delivery to the patient, the perfusion needs to be linked to the patient and never removed during surgery. It is required to ensure a proper connection of the cable to the patient during the entire surgery. Hence, there is the problem that health professionals need to direct their attention to the maintenance of continuous supply of the patient with perfusion or the like and cannot exclusively follow the surgery or any other interventional procedures. Therefore, the risk of any collision with an object connected to the object of interest, more particularly, the risk of pulling off a supply cable configured for infusion needs to be minimized There is further a risk of pain or discomfort of the patient, if an anaesthetic supply cable falls off due to movements of the C-arm. Moreover, tissue of the patient may be damaged due to uncontrolled tearing off a cable from an intravascular access. Due to collision with a C-arm member a mobile perfusion stand may tip over and fall on a medical health professional or the operation table, thus endangering an ongoing surgical intervention. Therefore, there is the need to prevent collisions with any objects as stands or supply cables connected to a patient.

Moreover, there is a need to optimise workflows of the health personnel, while ensuring the security of the patient. In summary, there is the need of the present disclosure to avoid any interference between a component of a moving C-arm and any object needed for safely supplying a patient with fluid or gas or a mixture thereof as required by the given conditions.

SUMMARY OF THE INVENTION

At least one of the embodiments of the present disclosure provides one or more solutions to the problems and disadvantages with the background art. Other technical advantages of the present disclosure will be readily apparent to one skilled in the art from the following description and claims.

In one aspect, the present disclosure is directed to a medical device for obtaining images of an object of interest such as a patient. The imaging device comprising an arc-shaped member, an assembly configured to support said arc-shaped member, wherein the arc-shaped member supports a radiation source on one end and on the other end a detector to scan an object of interest. Said assembly comprising a gantry with a rotatable support arm supporting at its end the arc shaped member, wherein at least one supply unit is mounted on the gantry connectable to a cable. Moreover, the supply cable is routed or guided in the vicinity or in the region of the axis of rotation of the support arm to be connected with the object of interest.

In another aspect, the present disclosure is directed to a method for supplying a medium to an object of interest such as a patient to be scanned by an imaging device comprising a movable arc-shaped member configured to support a radiation source on one end and a detector on another end to scan the object of interest, wherein the method comprises: connecting a cable to the object of interest such as patient; routing the cable from the object of interest through the region of the axis of rotation of the support arm of the arc-shaped member to a supply unit mounted on the gantry, supplying a medium from the supply unit comprised, in at least one embodiment, of a fluid (liquid or gas) to the object of interest via the cable; and rotating the radiation source and the opposed detector around the patient via a rotatable support arm.

The method can be performed in any order, for example, the connection to the object of interest can be performed after routing the cable. According to another embodiment of the disclosure the object of interest such as a patient can be first connected to a cable with a supply unit. Said supply unit can be mounted on the gantry without disconnecting the cable from the patient. Moreover, it is possible to mount a supply unit on the gantry before performing the above mentioned method steps. The method step of rotating can be performed discontinuously, whereas supplying a medium to the scanned object, the medium comprising fluid, gas or any other required medium is preferably performed continuously.

In another aspect of the present disclosure the cable is guided via a guiding unit mounted on the gantry in the vicinity of the rotatable support arm or via a cable guiding ring mounted on the rotatable support arm in the vicinity of the axis of rotation.

By using a guiding unit such as a ring the cable can be positioned such, that the cable is essentially routed into or at least in the vicinity of a region extending from the pivot point of the support arm along the rotational axis of the support arm to the object of interest. In other words the cable can be positioned close to the axis of rotation of the support arm. In the following it is considered that the region of the axis of the support arm comprises the axis of rotation of the support arm and the vicinity thereof.

The support arm performs rotary movements around the center of rotation that is to say around the axis of rotation. The rotation of the support arm around this fixed horizontal axis involves a motion of the C-arm and the parts secured thereto along a circular path around the object of interest. Due to the geometry of the C-arm and/or the support arm there is a space along the axis of rotation of the support arm extending between the rotating member and the object of interest, which is free of any moving object. This region is in the following called the "eye" of the C-arm, which constitutes the only space available in the vicinity of the imaging device for accessing the object of interest with a supply cable without colliding with the radiation source or the detector.

According to another aspect of the disclosure the supply unit can be selected from the group comprising a perfusion container, a respiratory device, an anaesthesia device, electrical power, monitoring unit and/or an injector device. In this way the object of interest such as a patient can continuously be delivered with air, infusion, drugs, medication or any other medium required for the object of interest. Further, the patient can be monitored by one or more signal cables. For example an electrocardiogram or other health parameters can be provided if sensors as electrodes are connected to the patient via at least one cable.

For example electrical power can be advantageously used for monitoring components or for pumps, which are adapted for providing precise flow rates of drugs or infusions. Moreover, mounting devices such a respiratory device comprising several components as a pumping system on the gantry can advantageously add weight, if the base of the medical device is not mechanically linked to the floor but for example wheel mounted. A wheel mounted medical device offers a particularly flexible form of mobility, because they are not linked to guidance facilities, but there is the need to ensure stability. By adding weight on the gantry positioned in the rear of the moving support arm, the stability of a wheel mounted medical device upon lateral C-arm movements can be enhanced. Thus, the C-arm imaging device is less susceptible to tipping, especially if the C-arm performs rotational or lateral movements along the rotational axis of the support arm. In general any weight addition or potential weight reduction with respect to the gantry is considered already in the conception of the machine. Thus, the components can be designed such, that stability can be ensured in any configuration.

According to yet another aspect of the present disclosure not only the C-arm but further the entire gantry is movable. In this way the x-ray source and detector can be selectively positioned relative to the length of the patient or and be moved aside if for a completion of a procedure nearly unobstructed access to the patient is required. For the mobile platform of the medical imaging device a retractable or a self-coiling retractable cable is provided, which can be extended and retracted according to the selected distance of the medical imaging device with regard to the object to be scanned.

One of the advantages, that is realized using the embodiments of the described embodiments, is to improve flexibility and workflow of the medical health personnel and to allow surgeons to focus on the procedure as emergency operations. Further, the present disclosure provides a C-arm device, which is simple in operation and at the same time ensures continuous medium supply of the object of interest such as a patient via at least one cable. If several supply units are required the number of cables may be increased accordingly.

Alternatively to an image acquisition device with one x-ray source and detector a bi-planar system comprising two radiation sources and respective detectors can be provided. As in the one-planar system the "eye" of the C-arm is preserved, leading to the advantage that at least one cable can be routed therein, without the risk of collisions. Further, the provision of one or more supply unit to the gantry of one medical imaging device can be used for upgrading an existing mobile imaging device. This upgrade results in a safe supply of the patient with a selected medium, while high quality images can be obtained at the same time. Various embodiments of the present application obtain only a subset of the advantages set forth. No one advantage is critical to the embodiments. Any disclosed embodiment may be technically combined with any other disclosed embodiment(s).

BRIEF DESCRIPTION OF THE DRAWINGS

The features and advantages of the disclosure will become apparent from a consideration of the accompanying drawings in which.

Figure 1:
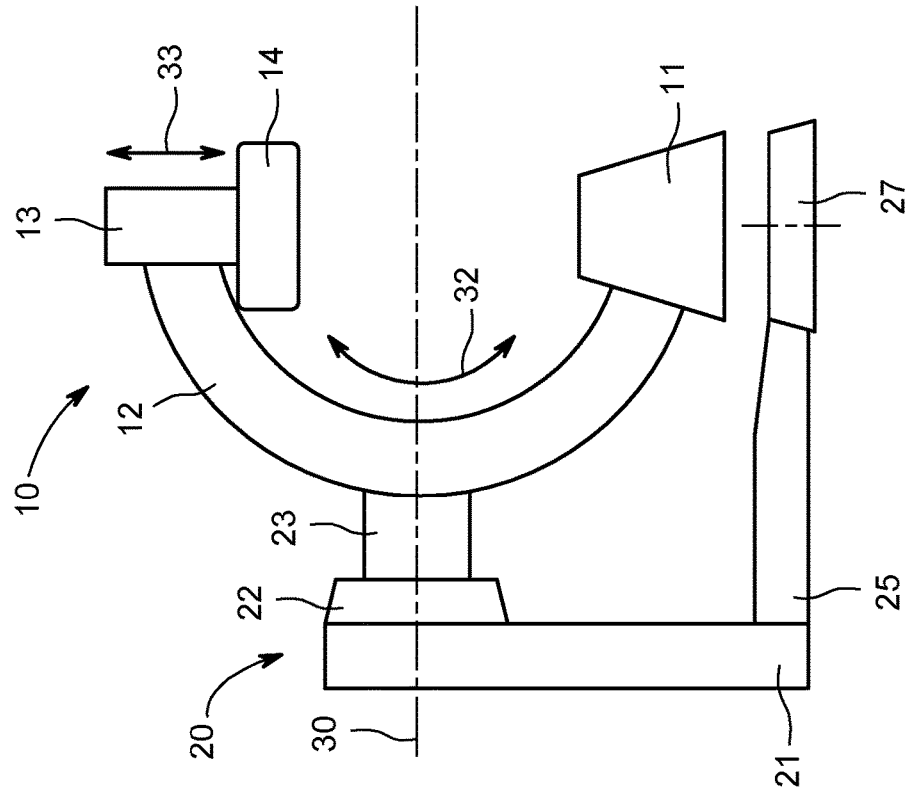
FIG. 1 is a diagrammatic illustration of the front view of an medical device utilising a C-arm with a radially outward extending support arm according to an exemplary embodiment of the disclosure.

It should be noted that these Figures are intended to illustrate the general characteristics of the devices and methods utilized in certain embodiments. However, the Figures are not to scale and may not precisely reflect the precise structure or performance characteristic of any given embodiment. Moreover, in the Figures like reference numerals designate corresponding parts throughout the different views or embodiments.

DETAILED DESCRIPTION

The present disclosure relates to the field of medical imaging devices and more particularly, to a device and method for supplying at least one medium to an object of interest, which is scanned by a mobile imaging device. In particular, the present disclosure relates to an imaging device comprising a movable C-arm with an x-ray system for scanning the object of interest such as a patient and a cable for supplying a perfusion or any other medium, such as a fluid medium (liquid and/or gas) to the object of interest.

A mobile C-arm device is diagrammatically illustrated in FIG. 1, wherein the medical device is generally marked with the reference numeral 10. The medical imaging device 10 includes an arc-shaped member 12 (C-arm). The so called C-arm 12 terminates in opposing distal ends. The C-arm 12 has preferably a uniformly circular C-shape that may alternatively comprise any arc-shaped member.

As can be seen in the front view of FIG. 1 the medical device 10 comprises a support arm 23 extending radially outwardly, whereas a radiation source 11 and a detector 14 are arranged on respective support units or assemblies 13, 15 and 16 such that their center lines are collinear with the vertical axis 35 in the shown position, which crosses the pivot point 34 of the rotating member 24. If the C-arm 12 rotates from the shown vertical position to a horizontal position either clockwise or counter-clockwise as shown by arrow 34, the centers of detector 14 and radiation source 11 will be arranged along the horizontal axis 36. In this way the C-arm can move around an object of interest. By pivoting round the pivot point 34 a rotational movement of preferably about 220° as indicated by the arrows 31 is performable. The detector 14 is preferably moved from the shown upward position about 90° to the right or left respectively. Following this movement the detector 14 and radiation source 11 can be positioned to the lateral side of the patient. Preferably the detector 14 is not positioned below the table. Thus, it can be ensured that essentially all radiation, which went through the patient, will be captured by the detector. In the shown position of FIG. 1 the support arm is extending to the right side of the gantry.

At the upper distal end of the C-arm the detector support unit 15 and a further support 13 for the detector 14 is shown. The support 13 for the detector is vertically movable as shown by arrow 33 in FIG. 2. With the option of vertical adjustment of the position of the detector 14, the width of the object to be scanned can be taken into account and the detector can be positioned as close to the object of interest as possible.

Figure 2:
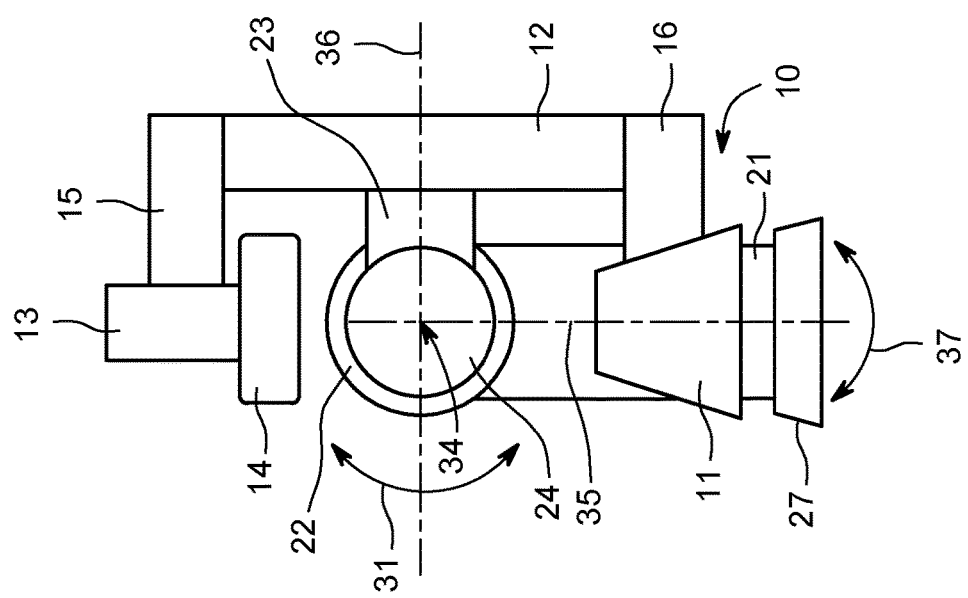
FIG. 2 is a side view of the medical device as shown in FIG. 1.

FIG. 2 shows a side view of FIG. 1. The mobile and rotating member 24 (see FIG. 1) is connected to the fixed holding unit 22. This holding unit 22 is attached on its rear side with the gantry 21. FIG. 2 shows further the footprint of the mobile C-arm imaging device 10. For the stability of the medical imaging device 10 the support structure 25 and the base 27 are arranged. In the illustrated embodiment the base 27 is connected to the floor, whereas the support structure 25 is pivotable and can rotate around a fixed point on the floor. This pivoting or panning movement is indicated by arrow 37.

The C-arm 12 cannot only move around the horizontal axis 30 extending through the pivot point 34 but also perform orbital movements along the arrow 32. These orbital movements are performable, since the C-arm 12 is configured to slide with regard to the support arm 23.

Figure 4:
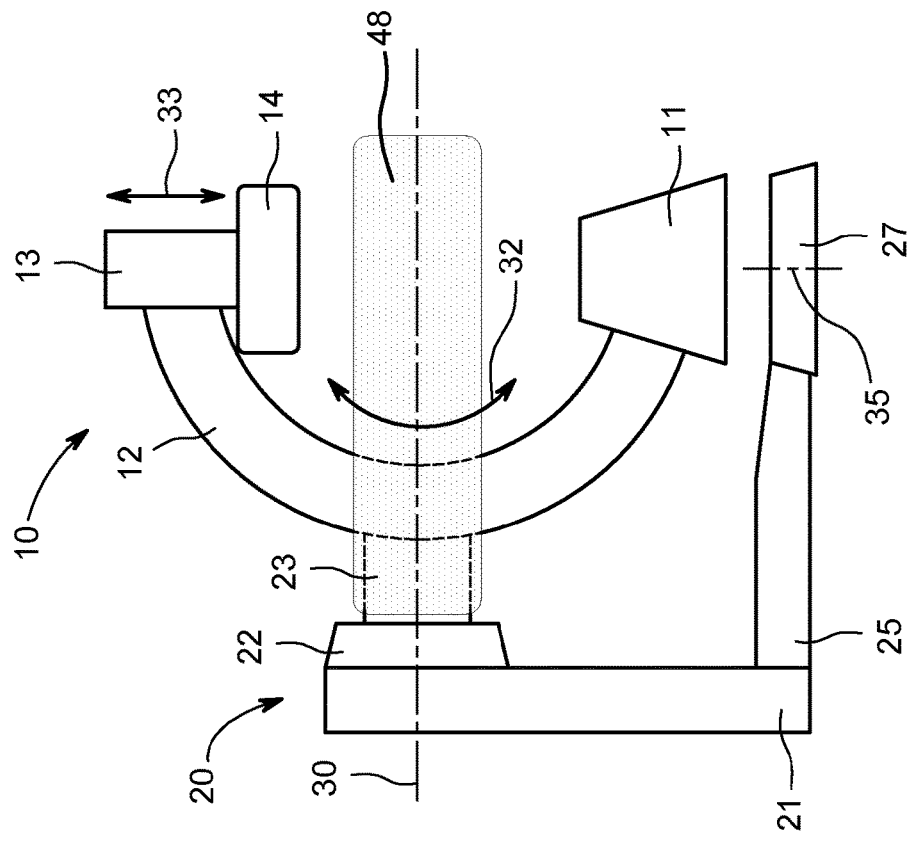
FIG. 4 is diagrammatically illustrating a side view of the "eye" of the C-arm shown in FIG. 3.
Figure 3:
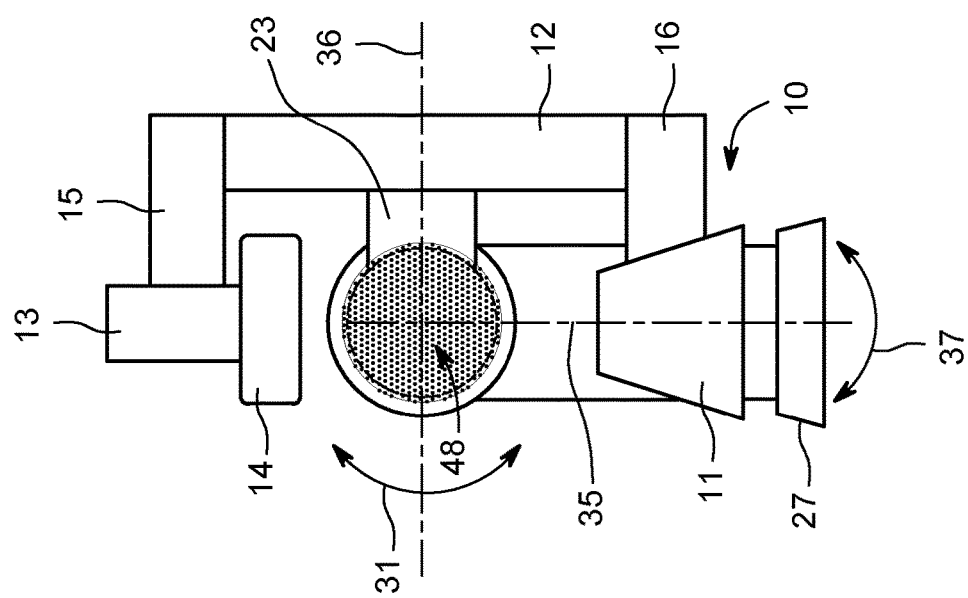
FIG. 3 is a front view of a C-arm device as shown in FIG. 1 diagrammatically illustrating a zone free of moving objects called the "eye" of the C-arm.
Figure 5:
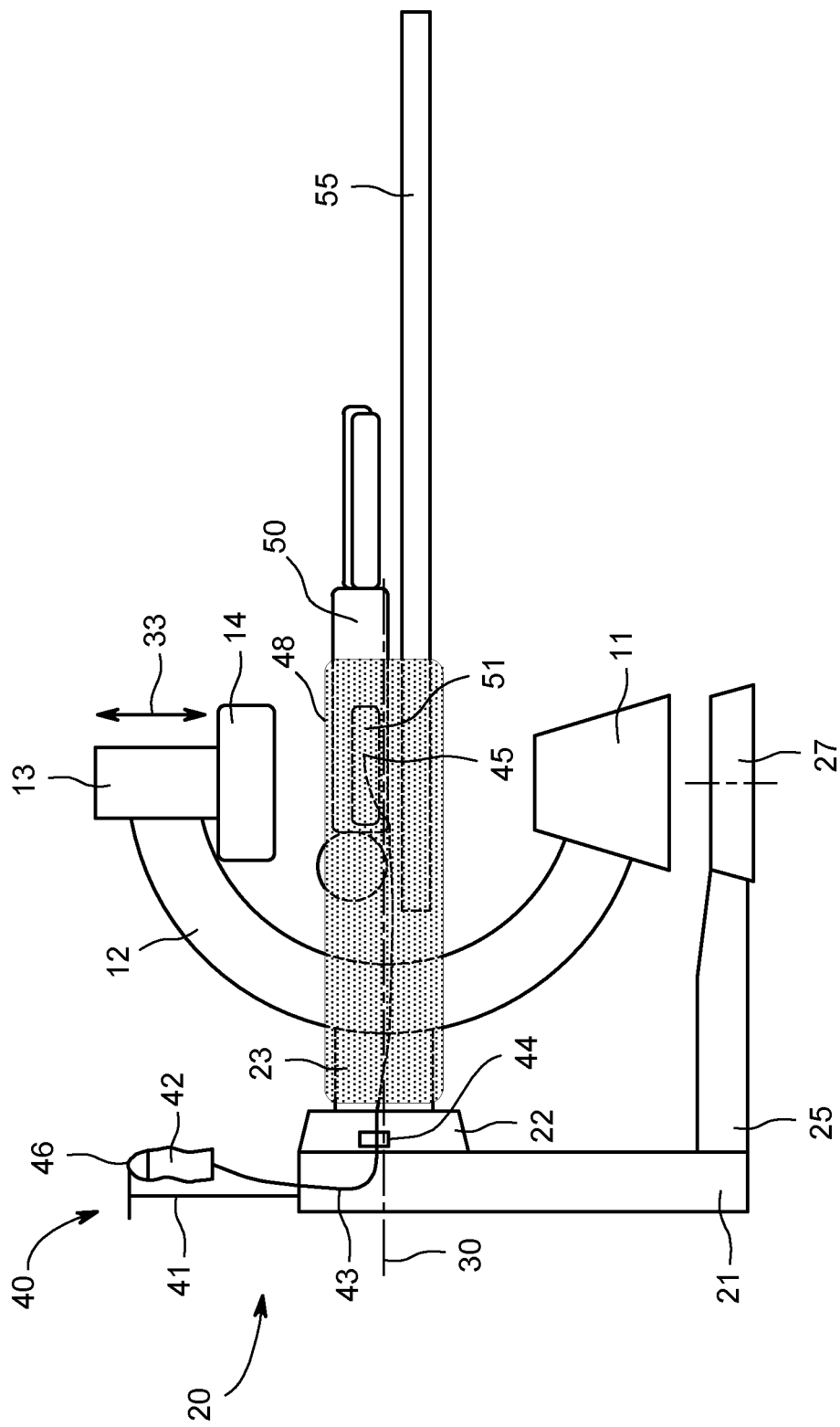
FIG. 5 is diagrammatically illustrating a lateral view of the medical device shown in FIGS. 3 and 4.

FIGS. 3, 4 and 5 show a medical imaging device 10 as shown in FIGS. 1 and 2, wherein further a zone free of any moving object or the so-called "eye" of the C-arm is illustrated. This region or eye of the C-arm 12 is indicated with the reference numeral 48. The cross-section of said eye of the C-arm 48 is indicated in FIG. 3 with grey shading and coincides substantially with the extension of the rotating member 24. The central point of the eye of the C-arm 48 coincides with the point of intersection of the vertical 35 and horizontal axis 36. FIG. 4 shows the lateral extension of the eye of the C-arm 48, which is free of any moving object of the medical imaging device 10.

FIG. 5 shows an exemplary embodiment in accordance with the present disclosure, wherein as part of a supply system 40 a perfusion container 42 is provided. For supplying a medium such as a perfusion liquid to an object of interest, a perfusion conduit, tube, or vessel 43 (hereinafter referred to as a "cable") is provided. On the stationary gantry 21, which is part of the support 20 for the arc shaped member, a pole 41 is mounted. The pole 41 comprises a suspension arrangement 46, which holds the perfusion container 42. The pole 41 aims to arrange a perfusion container above the head of the object of interest as a patient 50, in order to continuously deliver the fluid by gravity. In this way the use of a pump system is not necessary. A patient 50 can be positioned on a horizontal support like an operating table 55. The patient is connected to the perfusion cable 43 via a suitable connection element 45. Usually such connecting elements 45 are positioned intravascular in a part of the arm 51 of the patient 50.

The supply cable 43 is routed or guided by a guiding unit 44 into the vicinity of the eye of the C-arm 48. The guiding unit 44 is configured as a hook but may also have other suitable forms as a ring for reliably guiding the cable 43. Alternatively or in addition to the guiding unit 44 at least one more guiding unit (not shown) may be positioned on the gantry or the rotating member 24. Moreover, there may be a fixation unit (not shown) for the cable provided, which is arranged on the horizontal support or operating table 55. This fixation unit is preferably provided in case an enrolling system with a retractable cable is arranged on the gantry 21. Via said fixation unit, the force to retract the cable can be delimited to a desired cable section. That is to say the pulling force is only applied to the section extending from the enrolling system mounted on the gantry to the location of the fixation unit on the horizontal support for the patient. In this way the section of the cable extending from the fixation unit to the connecting element 45 of the patient can be loosely arranged. Thus, pulling off a cable 43 as an infusion cable from the arm of a patient 50 can be prevented.

The guiding units 44 can be configured at least partly flexible or rotatably attached, such that displacements of the cable due to movement of the patient or due to the rotation of the support arm can be compensated. As can be seen in the FIG. 5 the cable 43 has such a length that it is routed loosely through the guiding unit. Accordingly there is sufficient clearance such that the cable can be pulled through to a certain extent without hindrance. In this way, movements of objects linked to the cable as the patient's arm 51 can be compensated and an unintentional disconnection of the connecting element 45 can be avoided.

Figure 6:
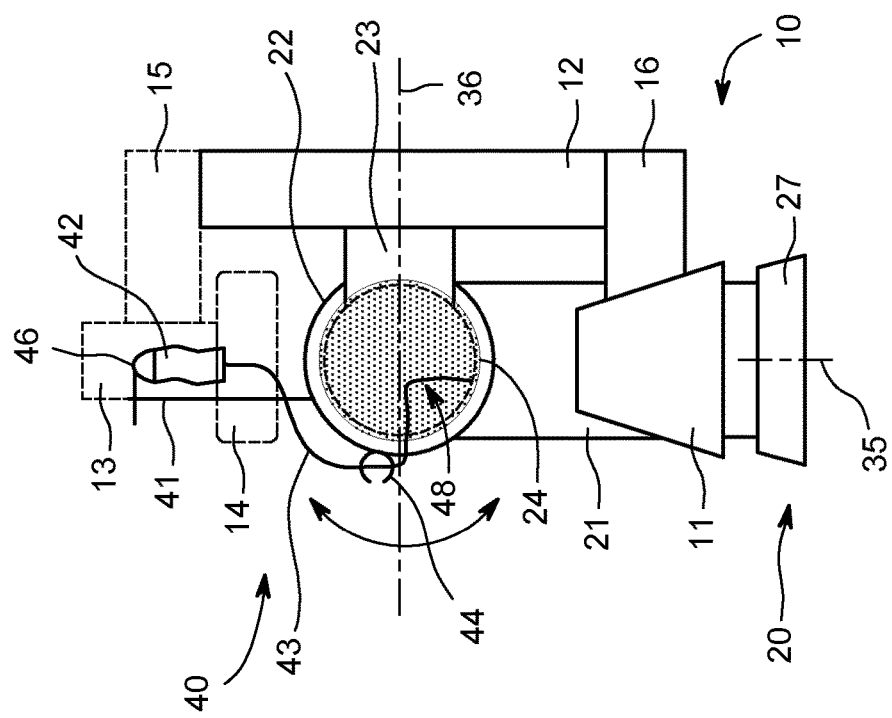
FIG. 6 is a front view of a C-arm device according to an exemplary embodiment of the disclosure.

FIG. 6 shows a front view of the medical imaging system 10 according to the embodiment shown in FIG. 5. The guiding unit 44 is positioned on the side (in FIG. 6 left), which is opposite of the position of the support arm 23 being horizontally arranged (extending to the right as shown in FIG. 6). The support arm 23 is not moved to the position of the cable guiding unit 44, since positions of the detector 14 below the horizontal axis are not desired for image acquisition. The guiding unit 44 is shown as a hook, which loosely guides the cable 43. In practice the perfusion container 43 can be already linked via a perfusion cable 43 to the arm 51 of the patient, when the patient is brought inside the surgical room. As soon as the patient is positioned on the operation table 55 in the surgery room, the health personnel can place the perfusion container 42 onto the pole 41 via the suspension arrangement 46. After hanging the perfusion container 42 on the pole 41 and routing the perfusion cable 43 through the hook 44, the patient can be scanned by the medical imaging device 10 without interrupting the supply of the patient 50 with a perfusion.

Due to the routing of the cable 43 in the eye of the C-arm the perfusion cable 43 will stay in region free of moving objects, when the C-arm 12 with the x-ray source 11 and detector 14 moves around the patient. Thus, there is no risk of interference between the perfusion cable 43 and components of the moving C-arm 12. The embodiment as illustrated in FIG. 6 has the advantage that the perfusion does not have to be removed from the patient 50. The C-arm can move rotationally over 360 degrees. There is no more risk of pulling off the perfusion cables 43 from the arm of a patient 50.

According to another embodiment of the disclosure the base 27 of the support structure 25 is configured to be moved with wheels attached to the base 27 (not shown). If such a mobile medical imaging device 10 moves away from the operation table axis, the pole 41 is moved with the gantry 21. Depending on the desired maximum displacement of the medical imaging system 10 with respect to the operating table 55, the cable 43 is provided with the respective length or configured as retractable cable. A retractable cable may be arranged such that it coils about a device mounted on the gantry 21. In this way entanglement with parts of the cable not rolled up, can be avoided. A retractable cable is also advantageous in case the table 55 is movable in relation to the medical device.

Figure 7:
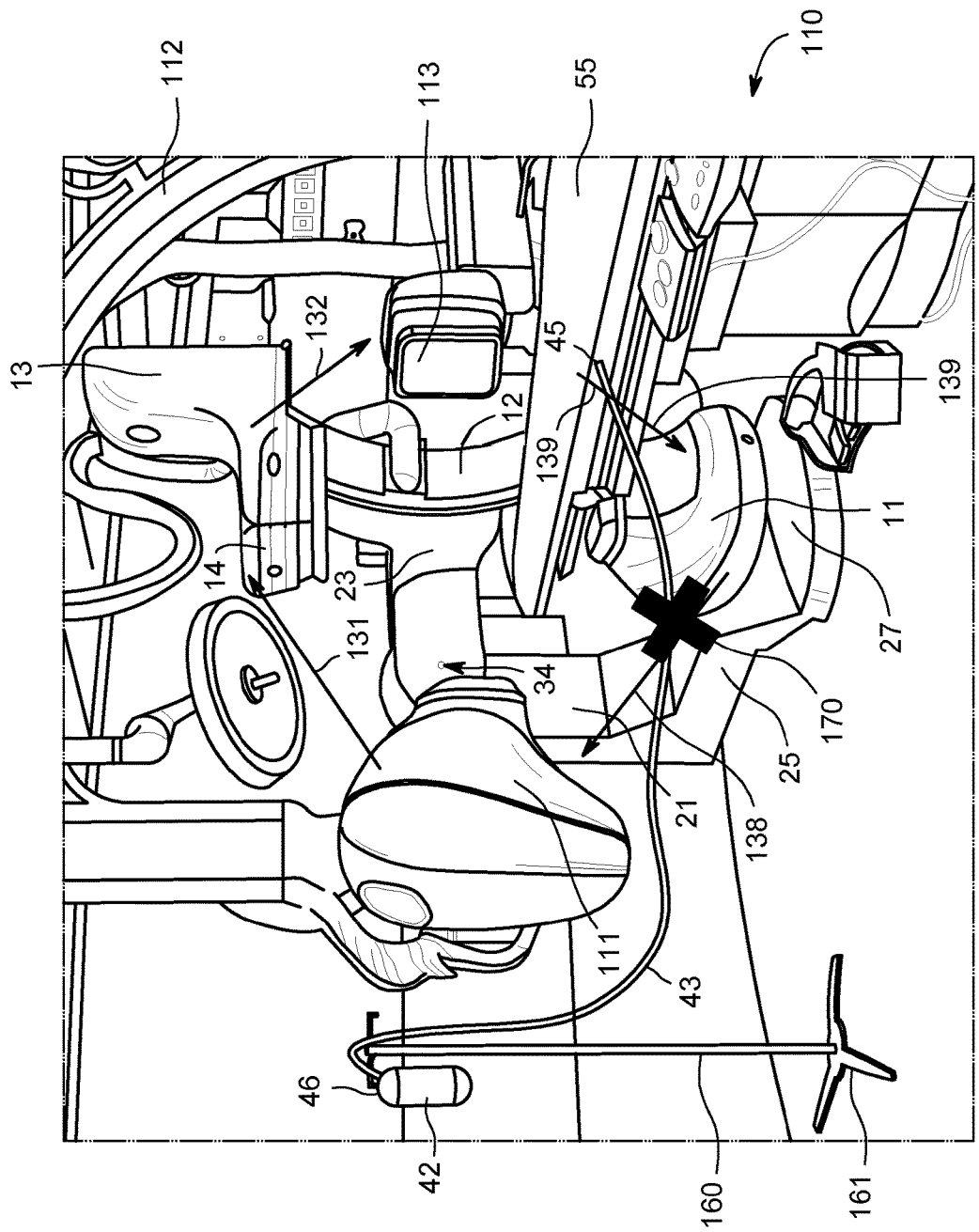
FIG. 7 is a diagrammatic illustration of a bi-planar image acquisition device with an external perfusion stand.

FIG. 7 shows a bi-planar medical imaging system 110 with an additional radiation source and detector. FIG. 7 shows a perfusion stand 160 which has a mobile support structure 161. On the stand 160 a suspension 46 is arranged to hold a perfusion container 42. The bi-planar medical imaging system 110 comprises two radiation sources 11 and 111 and two corresponding detectors 14 and 114. The additional or second radiation source 111 and detector 114 are mounted on the ceiling (not shown). The C-arms 12 and 112 can be moved in a clockwise or counter clockwise direction. The arrows 131, 132, 139 and 138 in FIG. 7 mark a clockwise rotational movement of the respective components of the two C-arms 12 and 112. Due to routing the cable 43 to the externally positioned stand 160, there is the problem that after the indicated clockwise movement the radiation source 11 collides with the perfusion cable 43. This collision risk is schematically illustrated by cross 170. After such a collision the perfusion cable 43 may fall off the patient or the stand 160 may fall down, thus the procedure of supplying the infusion liquid may be interrupted.

Figure 8:
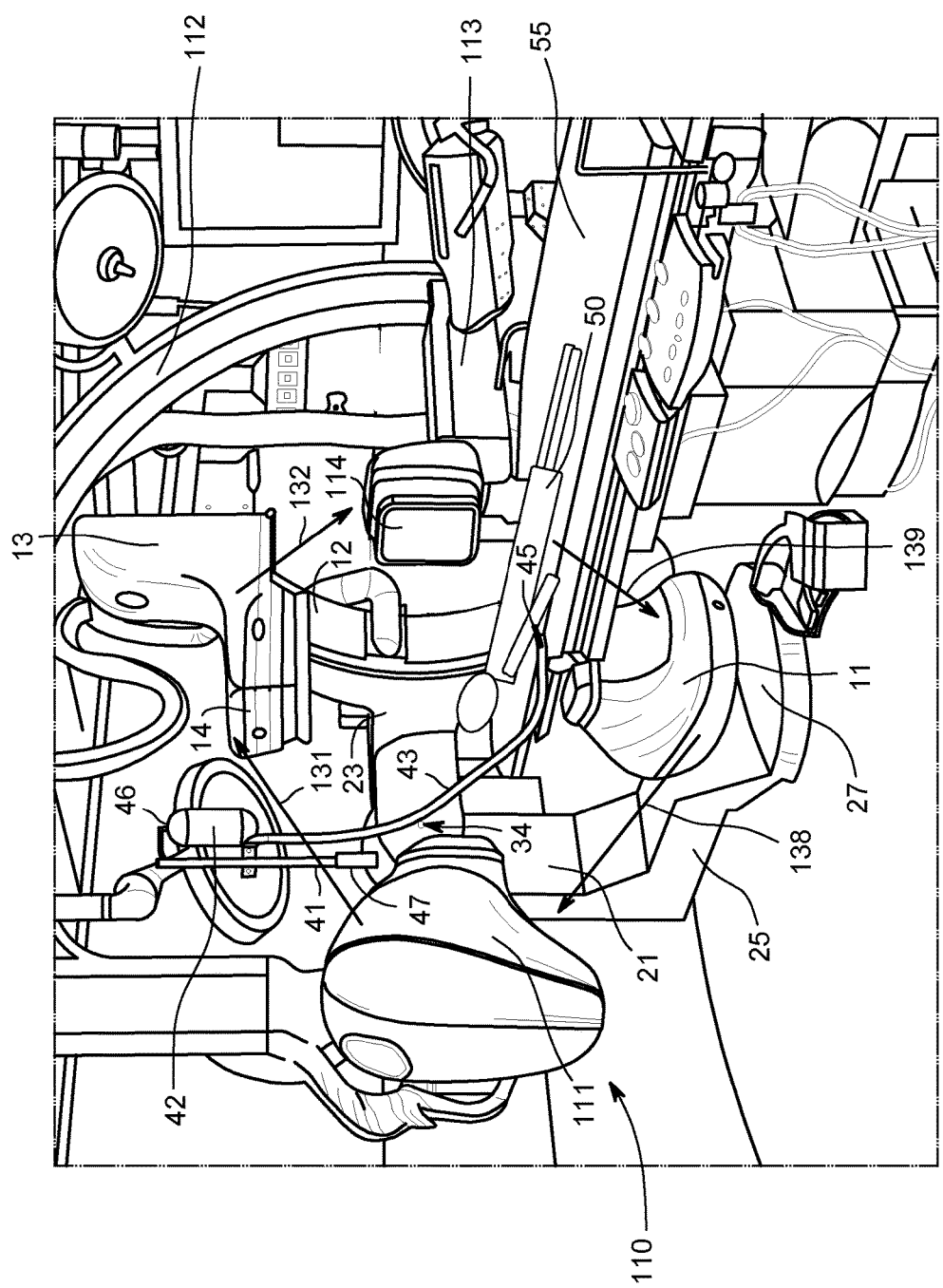
FIG. 8 is a 3-dimensional illustration of a bi-planner image acquisition device according to another exemplary embodiment of the present disclosure.

FIG. 8 shows an embodiment according to the disclosure, wherein a perfusion container 42 as supply unit is not arranged in the outer periphery of the medical system 110 but on the gantry 21 of the bi-planar medical imaging device 110. In particular the perfusion container 42 is mounted on a suspension arrangement 46, which is an integral part of the pole 41 fixedly connected to the stationary gantry 21 of the imaging device 110.

FIG. 8 further illustrates the routing of the cable 43 along the pivot point 34 of the support arm. The rotating centre of the C-arm 12 coincides with the pivot point 34. The cable 43 is connected via a connecting element 45 to the patient 50. In this way safety for the patient 50 can be ensured and the healthcare personnel can concentrate on interventions or other procedures. This arrangement improves flexibility and ease of movement for the healthcare personnel.

Figure 9:
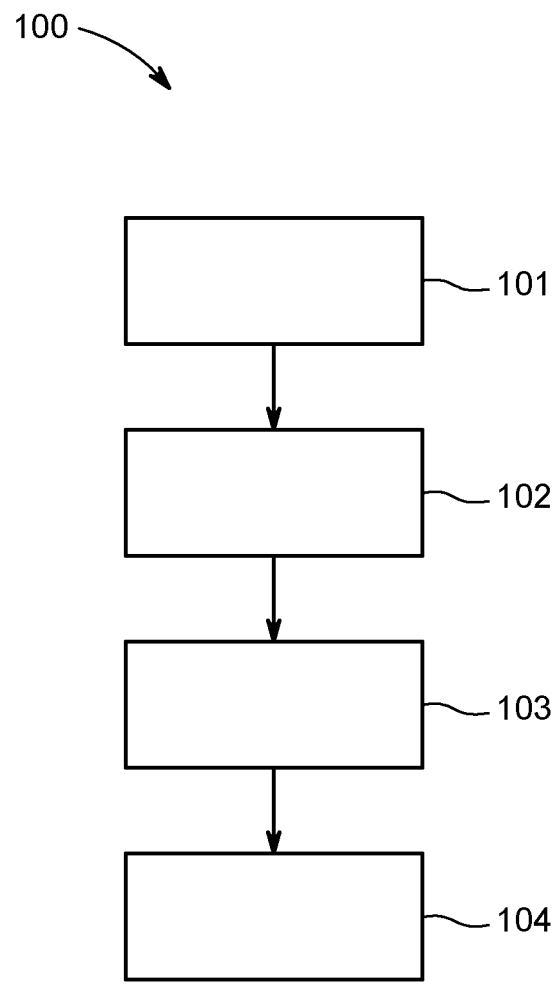
FIG. 9 shows a flow chart of the method for positioning.

FIG. 9 shows a flow chart according to a method 100 for supplying a medium to an object interest to be scanned by an imaging device 10 comprising a movable arc-shaped member configured to support a radiation source 11 on one end and a detector 14 on another end to scan an object of interest such as a patient, wherein the method comprises the following steps: According to a first method step 101 a cable 43 is connected to the object of interest such as a patient. Then routing of the cable 43 from the object of interest through the region of the axis of rotation of the support arm to a supply unit mounted on the gantry is performed in a second method step 102. These first two method steps 101 and 102 are interchangeable in its order. In method step 103 a medium from the supply unit comprising fluid or gas is supplied continuously or discontinuously to the object of interest via the cable. For example if drugs instead of an infusion are delivered by the supply unit a discontinuous supply may be prescribed by a health professional. In method step 104 the radiation source and the opposed detector are rotated around the object of interest such as a patient via a rotatable support arm 23. The method step 104 of rotating of the mobile C-arm 12 is performed if the medical imaging device is required to change its position and the health professional needs another angle for acquiring further x-ray images. According to the present disclosure method steps 103 and 104 can be performed simultaneously.

Moreover the method may further comprise an additional step of mounting a supply unit configured as a perfusion container on the gantry using a suspension arrangement of a pole, which is fixedly arranged on the gantry. Said method step can be done before a patient is connected to the supply cable or afterwards.

This written description uses examples to disclose the invention, including the best mode, and also to enable any person skilled in the art to practice the invention, including making and using any devices and performing any incorporated methods. The patentable scope of the invention is defined by the claims, and may include other examples that occur to those skilled in the art.

What is claimed is:

1. A medical imaging device comprising:
   a radiation source;
   a detector;
   an arc-shaped member configured to support the radiation source on one end and the detector on another end;
   an assembly configured to support said arc-shaped member, the assembly comprising a gantry with a rotatable support arm supporting at one end the arc-shaped member;
   at least one supply unit mounted to the gantry; and
   a conduit in fluid communication with the at least one supply unit at one end and configured to be connected directly or indirectly to an object of interest at another end, the conduit being routed from the at least one supply unit through a region of an axis of rotation of the support in order to be connected with the object of interest.

2. A medical imaging device according to claim 1, wherein the conduit is guided via a guiding unit mounted on the gantry in the vicinity of the rotatable support arm.

3. A medical imaging device according to claim 1, wherein the conduit is fixable by a fixation unit arranged on a horizontal support for the object of interest.

4. A medical imaging device according to claim 1, wherein the support arm extends radially outwardly with respect to the axis of rotation of the support arm.

5. A medical imaging device according to claim 1, wherein the at least one supply unit is a perfusion container.

6. A medical imaging device according to claim 5, wherein the perfusion container is connected to the gantry by a pole or support structure.

7. A medical imaging device according to claim 1, wherein at least one of the at least one supply unit is a respiratory device.

8. A medical imaging device according to claim 1, wherein at least one of the at least one supply unit is an anaesthesia device.

9. A medical imaging device according to claim 1, wherein at least one of the at least one supply unit is an injector device.

10. A medical imaging device according to claim 1, wherein the at least one supply unit further provides electrical power for electrically driven supply units.

11. A medical imaging device according to claim 1, wherein the gantry is movable and the conduit is retractable toward one of the object of interest and the at least one supply unit.

12. A medical imaging device according to claim 11, wherein the retractable conduit is self-coiling.

13. A medical imaging device according to claim 1, further comprising:
   an additional radiation source;
   an additional detector; and
   an additional arc-shaped member configured to support said additional radiation source on one end and said additional detector on another end.

14. A medical imaging device according to clam 1, wherein the object of interest is a patient.

15. A method for supplying a medium to an object of interest to be scanned by an imaging device with a movable arc-shaped member configured to support a radiation source on one end and a detector on another end, the method comprising:
   connecting a conduit directly or indirectly to the object of interest;
   routing the cable from the object of interest through the region of the axis of rotation of the support arm of the arc-shaped member to a supply unit mounted on a gantry,
   supplying a medium from the supply unit to the object of interest via the conduit; and
   rotating the radiation source and the opposed detector around the object of interest via the rotatable support arm with the conduit routed through the region of the axis of rotation.

16. A method according to claim 15, further comprising:
   mounting a supply unit configured as a perfusion container on the gantry using a suspension arrangement which is fixedly arranged on the gantry.

17. A method according to claim 15, wherein the object of interest is a patient.

* * * * *